United States Patent [19]

Truesdale

[11] Patent Number: 4,598,160
[45] Date of Patent: Jul. 1, 1986

[54] INTERMEDIATE PHENOLIC COMPOUNDS FOR THE CATALYTIC SYNTHESIS OF CHROMANS

[75] Inventor: Larry K. Truesdale, Nutley, N.J.

[73] Assignee: Hoffmann-La Roche Inc., Nutley, N.J.

[21] Appl. No.: 710,193

[22] Filed: Mar. 11, 1985

Related U.S. Application Data

[60] Continuation of Ser. No. 514,134, Jul. 15, 1983, abandoned, which is a division of Ser. No. 372,858, Apr. 28, 1982, abandoned.

[51] Int. Cl.[4] .................... C07C 69/773; C07C 39/19
[52] U.S. Cl. .................................. 560/144; 549/416; 549/411; 549/408; 260/395; 556/449; 560/109; 568/766; 568/650; 568/646; 568/640; 568/592

[58] Field of Search .............. 549/408, 416, 411; 568/766, 592, 650, 646, 640; 560/144, 109; 556/449; 260/395

[56] References Cited

U.S. PATENT DOCUMENTS

| 2,270,634 | 1/1942 | Isler | 568/766 |
| 3,354,181 | 11/1967 | Gloor et al. | 549/411 |
| 3,646,222 | 2/1972 | Kawamatsu et al. | 568/766 |

Primary Examiner—Nicky Chan
Attorney, Agent, or Firm—Jon S. Saxe; George M. Gould; Patricia A. Coburn

[57] ABSTRACT

A catalytic synthesis of chromans in racemic or optically active forms, including intermediates thereto; the synthesis employs an asymmetric palladium (II) catalyzed oxidative cyclization of a 2-homoallylphenol and provides intermediates useful in making chromans, especially vitamin E in racemic or optically active forms.

5 Claims, No Drawings

INTERMEDIATE PHENOLIC COMPOUNDS FOR THE CATALYTIC SYNTHESIS OF CHROMANS

This is a continuation of application Ser. No. 514,134 filed July 15, 1983, now abandoned, which is a divisional application of Ser. No. 372,858, filed Apr. 28, 1982, now abandoned.

BACKGROUND OF THE INVENTION

In the past, optically active α-tocopherol (Vitamin E) and derivatives thereof which are the 2R,4′R,8′R isomers of compounds of the formula:

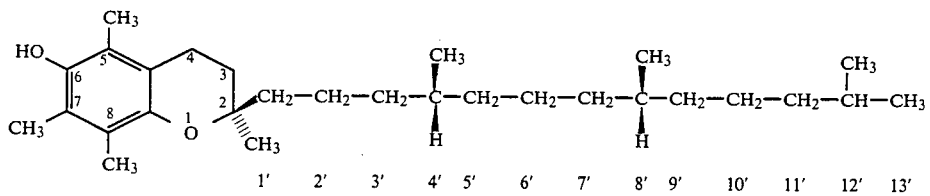

have been prepared through isolation from natural sources such as vegetable oil. This procedure suffers from many drawbacks due to the fact that the tocopherol content of these oils is very small. Therefore, a great amount of oil must be processed in order to isolate a small amount of natural alpha-tocopherol. Additionally, the process whereby various tocopherols are isolated from vegetable oil is extremely cumbersome.

In U.S. Pat. No. 4,113,740 there is disclosed the synthesis of a compound of formula I by coupling a hydroxy protected chromanol aldehyde with a 3R, 7R alkyl phosphonium halide in a Wittig reaction to provide the three centers of chirality in the final product. This is a difficult synthesis in that it requires optically pure fragments chemically resolved in order to introduce three centers of chirality in a compound of formula I.

It has been determined, however, in rat fetal resorption tests that the biological potency of (2R,4′RS,8′RS)-alpha-tocopherol of the formula

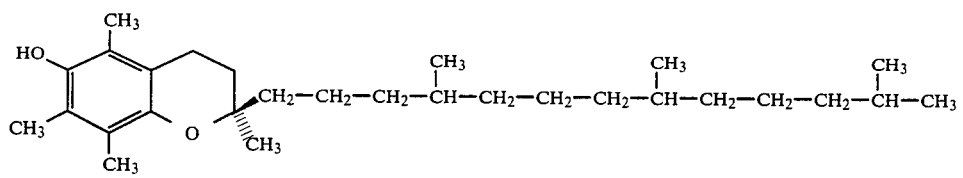

having only one chiral center, is identical to that of natural Vitamin E, i.e. (2R,4′R,8′R)-α-tocopherol of formula I which has three centers of chirality.

SUMMARY OF THE IVENTION

In accordance with this invention, a new synthesis, including new intermediates thereto, is provided for converting E and Z isomers of a compound of the formula

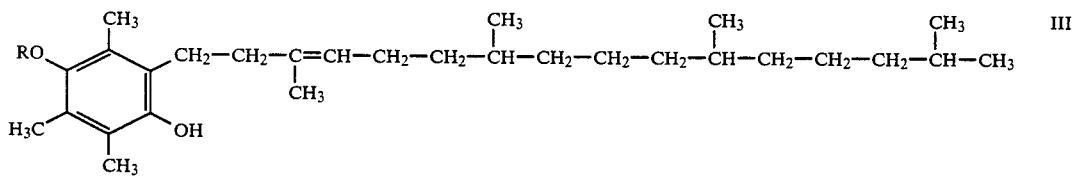

Attempts to produce optically active alpha-tocopherol, i.e. 2R,4′R,8′R isomers, synthetically have been difficult because such a compound has three centers of chirality. Optically inactive alpha-tocopherol, i.e. 2RS,4′RS,8′RS isomers, have been prepared and found to be biologically useful, but the biological potency is less than that of the optically active compounds of formula I.

wherein R represents hydrogen or, taken together with its attached oxygen atom, represents an ester protecting group removable by hydrolysis or ether protecting group removable by hydrogenolysis or acid catalyzed cleavage, to a racemic (2RS) compound of the formula

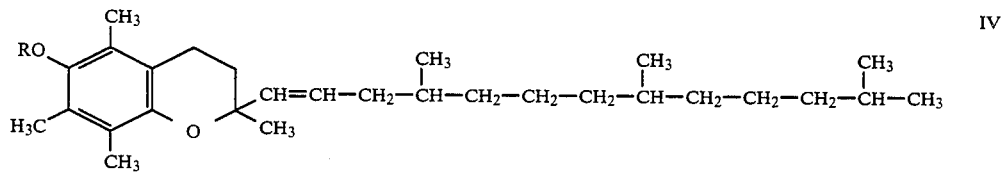

wherein R is as described above;
or to an asymmetric (2R) compound of the formula

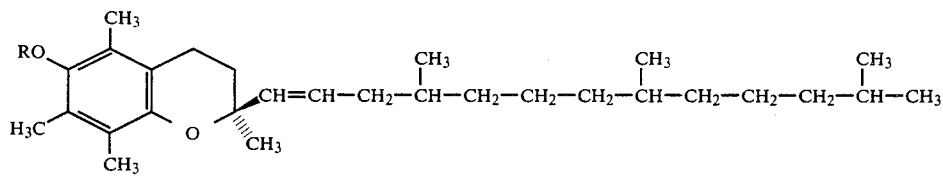

V wherein R is as described above;
or to the asymmetric (2S) compound of the formula

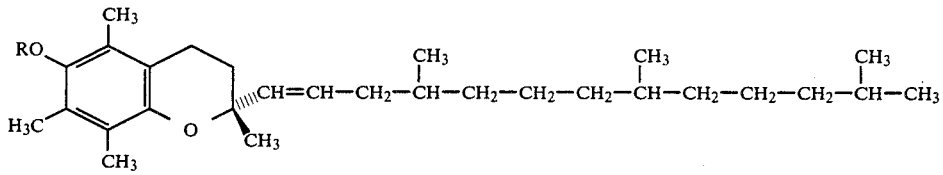

V' wherein R is as described above,
by treating the compound of formula III with a π-allyl palladium (II) complex and a copper salt as co-catalysts.

The chirality at the 2-position in isomers of compounds of formulae V and V' or the racemic mixture (2RS) in a compound of formula IV can be produced as desired depending on the isomeric form of the π-allyl palladium (II) complex being used as a co-catalyst.

DETAILED DESCRIPTION OF THE INVENTION

In the pictorial representation of the compounds given throughout this application, a ( ▮ ) tapered line indicates a substituent which is pointed out of the plane of the paper towards the reader and the ( ≡ ) multiple lines indicate a substituent which is pointed into the plane of the paper away from the reader. The dotted line indicates a three center, four electron donor bond or its tautomeric σ-allyl form.

As used throughout this application, the term "lower alkyl" includes both straight and branched chain saturated hydrocarbon groups containing from 1 to 7 carbon atoms such as methyl, ethyl, propyl, isopropyl, etc. The term "halogen" or "halo" includes all four halogens, such as bromine, chlorine, fluorine and iodine.

The term "lower-alkoxy" as used throughout the application denotes lower alkoxy groups containing from 1 to 7 carbon atoms such as methoxy, ethoxy, propoxy, isopropoxy, etc. The term "lower-alkanoyl" denotes lower-alkanoyl groups containing from 2 to 6 carbon atoms such as acetyl or propionyl. The term "aryl" designates mononuclear aromatic hydrocarbon groups such as phenyl, tolyl, etc. which can be unsubstituted or substituted in one or more positions with a lower-alkylenedioxy, a halogen, a nitro, a lower-alkyl or a lower-alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups. The term "aryl-lower-alkyl" comprehends groups wherein aryl and lower-alkyl are as defined above, particularly benzyl.

As still further used herein, the term "ester protecting group removable by hydrolysis" means any conventional organic acid ester protecting group which can be removed by hydrolysis.

The term "ether protecting group removable by hydrogenolysis or acid catalyzed cleavage" designates any ether which, upon acid catalyzed cleavage or hydrogenolysis yields the hydroxy group. A suitable ether protecting group is, for example, the tetrahydropyranyl ether or 4-methyl-5,6-dihydro-2H-pyranyl ether. Others are arylmethyl ethers such as benzyl, benzhydryl or trityl ethers or alpha-lower-alkoxy-lower-alkyl ether, for example, methoxymethyl or allylic ethers or trialkyl silyl ethers such as trimethyl silyl ether or dimethyl-tert.-butyl silyl ethers. Other ethers which are preferred are tertiary butyl ethers.

The preferred ethers which are removed by acid catalyzed cleavage are t-butyl and tetrahydropyranyl. Acid catalyzed cleavage can be carried out by treatment with a strong organic or inorganic acid. Among the preferred inorganic acids are the mineral acids such as sulfuric acid, hydrohalic acid, etc. Among the preferred organic acids are lower alkanoic acids such as acetic acid, trifluoroacetic acid, etc. and arylsulfonic acids such as para-toluene sulfonic acid, etc. The acid catalyzed cleavage can be carried out in an aqueous medium or in an organic solvent medium. Where an organic acid is utilized, the organic acid can be the solvent medium. In the case of t-butyl, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The preferred ethers which are removable by hydrogenolysis are the aryl methyl ethers such as benzyl or substituted benzyl ethers. The hydrogenolysis can be carried out by hydrogenation in the presence of a suitable hydrogenation catalyst. Any conventional method of hydrogenation can be utilized in carrying out this procedure. Any conventional hydrogenation catalyst such as palladium or platinum can be utilized.

In accordance with this invention, a compound of formula III (which consists of the isomeric compounds of formulae III' and III'') is produced and thereafter converted to a compound of formulae IV or V in accordance with the reaction steps designated A–E in the following Reaction Scheme:

Reaction Scheme

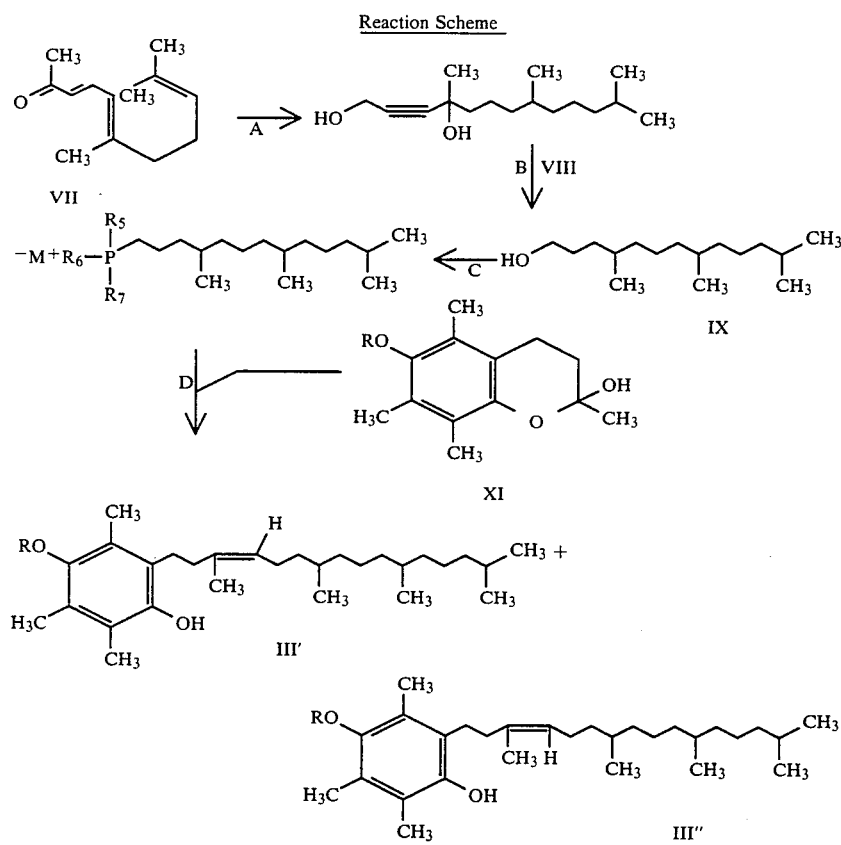

III' or III" —E→ IV or V wherein M represents halogen; $R_5, R_6, R_7$ separately represent lower-alkyl, lower-alkoxy or aryl; and R is as defined earlier.

The starting material of the foregoing reaction scheme is pseudo-ionone, the compound of formula VII which can be converted to 4,8,12-trimethyltridec-2-yn-1,4-diol, a compound of formula VIII which, in turn, can be converted to the alkyl alcohol compound of formula IX, i.e. 4,8,12-trimethyltridecanol, by methods known per se; as for example by the procedure of Sato et al., J. Org. Chem. 28, 45 (1963).

More particularly, the compound of formula VII can readily be converted to the compound of formula VIII in step A by catalytic hydrogenation of the compound of formula VII, followed by ethynylation to produce the triple bond of compound VIII with the three additional carbon atoms. Any conventional method of catalytic hydrogenation can be employed. Among such methods there are preferred those in which the conventional hydrogenation catalyst is a noble metal such as palladium or platinum or compounds thereof, the most preferred being palladium supported on an inert carrier material such as $CaCO_3$. The catalytic hydrogenation is preferably carried out in a protic solvent as for example an alcohol, preferably ethanol. In carrying out this conversion, temperature and pressure are not critical and either room temperature and atmospheric pressure or elevated or reduced temperatures and pressures can be used. The preferred temperature, however, is room temperature. Furthermore, in carrying out this conversion, the amounts (concentrations) of the components in this reaction step, i.e. starting material, catalyst, solvent and base, are not critical, and any effective amounts capable of producing the compound of formula VIII may be employed.

The ethynylation can be carried out in a conventional manner known per se. For example, ethynylation can be effected by treating the resulting hydrogenated compound derived from formula VII with propargyl alcohol and a base such as potassium or sodium hydroxide or a lower alkyl lithium base such as butyl lithium. The reaction is preferably run in an ethereal solvent such as tetrahydrofuran.

After the compound of formula VIII has been formed in Step A, the compound of formula VIII, the desired product, may be purified by any conventional purification method. It is preferred that the desired product be purified or isolated by vacuum distillation, retaining the distillate which contains the desired product.

The compound of formula VIII can be converted to the compound of formula IX in Step B by dehydrating and hydrogenating. Any conventional method for removing an hydroxy group adjacent to a carbon-carbon triple bond and hydrogenating the triple bond may be employed. The compound of formula IX can be formed by treating the compound of formula VIII with a dehydrating agent such as potassium bisulfite in an inert, high boiling solvent such as p-xylene, followed by hydrogenation of the dehydration product. This hydrogenation can be carried out, for example, with hydrogen and Raney nickel at elevated temperature and pressure, preferably 60°–100° C. and 1500–2000 psi.

The desired product, i.e. the compound of formula IX, can be purified or isolated by conventional methods such as vacuum distillation.

The compound of formula IX is converted to the compound of formula X, i.e. 4,8,12-trimethyltridecyl phosphonium halide in Step C by halogenation, followed by conversion to a phosphonium salt. Any conventional method of converting an alcohol to a halide can be utilized to carry out this reaction. More particularly, any of the conventional halogenating agents known to halogenate an alcohol by replacing the hydroxy group of the alcohol with a halogen can be used. Among these conventional halogenating agents there are included hydrogen bromide, thionyl bromide, phosphorous pentabromide and triphenylphosphine dibromide, with the latter being preferred to provide the preferred compound, i.e. 1-bromo-4,8,12-trimethyltridecane. Any of the conditions conventionally utilized with these halogenating agents can be used to carry out this reaction. The phosphonium salt can be formed by any conventional method known per se. Any phosphonium salt may be formed, such as, for example, 4,8,12-trimethyl-tridecyl-triphenyl phosphonium bromide. The desired product, i.e. compound of formula X, can be purified or isolated by conventional methods such as crystallization, but it is preferred that Step D follow without isolation of the compound of formula X.

The compounds of formulae III' and III" are produced in Step D via a Wittig reaction by coupling the compound of formula X with a compound of formula XI. Any of the conditions conventional in a Wittig reaction can be utilized to carry out this coupling. The compounds of formulae III' and III" are ortho-substituted homoallylic phenols and represent olefinic isomers (E and Z), i.e. the compound of formula III, which can be separated by a conventional separating method, such as for example high pressure liquid chromatography, to provide the compounds of formula III' and III".

The starting materials in step E can be a compound of formula III', III" or III. Where it is desired to produce the compound of formula IV (a racemic mixture), either the compounds of formula III', III" or III can be utilized. On the other hand, where it is desired to produce the compound of formula V, the compound of formula III" can be utilized.

A compound of formula III' or of formula III may be converted to a compound of formula IV in step E by treatment of the compound of formula III' or of formula III with a $\pi$-allyl palladium (II) complex and a copper salt as co-catalysts in the reaction mixture.

A compound of formula III" can be converted to a compound of formula IV or V in step E by treatment of the compound of formula III" with a $\pi$-allyl-palladium (II) complex and a copper salt as co-catalysts in the reaction mixture.

The $\pi$-allyl-palladium (II) complex may be any conventionally recognized chiral palladium complex. For example, such complexes include compounds of the formula

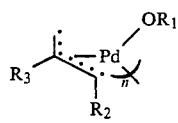

wherein n is 1 or 2; $R_1$ taken together with its attached oxygen atom represents lower-alkanoyl, halo-lower-alkanoyl, lower-alkoxy or hydroxy; $R_2$ and $R_3$ represent hydrogen or lower-alkyl or taken together form a 5 or 6 membered cyclic hydrocarbon; and the dotted line represents a tautomeric bond to provide either $\alpha$ or $\beta$ olefinic isomers,
and compounds of the formula

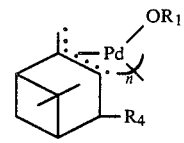

wherein n, $R_1$ and the dotted line are as previously described and $R_4$ represents hydrogen or lower-alkyl or lower-alkanoyl or alkoxy.

Of the conventional complexes, the chiral palladium pinene complex such as palladium-$\beta$-pinene or palladium-$\alpha$-pinene are preferred, and especially preferred is substituted palladium-$\beta$-pinene complex such as Bis-[eta/3/-7,7-dimethyl-4-methylenebicyclo-[3.1.1]hept-3-yl]bis[mu-(trifluoroacetato-O:O)]dipalladium.

Either a palladium-$\beta$-pinene complex or a palladium-$\alpha$-pinene complex can be employed in converting a compound of formula III' or of formula III to a compound of formula IV in step E.

A palladium-$\beta$-pinene complex can be employed in converting a compound of formula III" to a compound of formula V in step E.

The amount of the chiral palladium pinene complex employed to carry out step E may be any catalytically effective amount. This amount preferably is from 0.01 to 0.5 equivalents of the starting material for step E, with the most preferred being from 0.1 to 0.01 equivalents.

The copper salt employed also as co-catalyst in Step E may be any conventional copper salt. Among such conventional copper salts there are included for example copper halides such as copper chloride, copper bromide, copper fluoride and copper iodide, copper aroylate such as copper benzoate, copper-lower-alkanoyl such as copper acetate. The preferred copper salt is $Cu(OAc)_2$. The amount of copper salt employed as catalyst in step E may be any catalytically effective amount. This amount preferably is from 1–100% equivalents of the starting material, with the most preferred being from 10% to 500%.

In the conversion of the starting material in Step E, an inert solvent can be employed such as an organic solvent. Among such solvents there is included alcohols having 1-12 carbon atoms. The preferred alcohol is isopropanol.

The reaction represented by Step E is an oxidation reaction. In carrying out such a reaction, temperature and pressure are not critical and either room temperature and atmospheric pressure or elevated or reduced temperature and pressure can be used. It is preferred that the reaction be carried out at elevated temperatures between 30°–50° C., especially preferred is 35° C., and at atmospheric pressure to 50 psi, especially preferred is 10–20 psi. The reaction can be carried out under an atmosphere of oxygen or an oxygen containing substance such as air, with pure oxygen preferred. The amount of oxygen is not critical. Any effective amount of oxygen or oxygen-containing substance may be employed to carry out the oxidation. It is preferred that an excess of oxygen be used per equivalent of starting material in step E.

The reaction of Step E can be carried out by mixing all the starting material, catalysts solvent and oxygen-containing substance in combination at the preferred temperature and pressure, or by adding each ingredient separately. It is preferred that the reaction of Step E be carried out by adding the starting material and catalysts to the solvent and then adding the oxygen or oxygen-containing substance last.

Compounds of formula IV or V are produced by Step E. Compounds of formula IV (an isomeric mixture) may be resolved into the isomers by any conventional resolving methods such as conventional HPLC methods. Compounds of formula V or the optically active resolved isomers of formula IV may be converted to a compound of formula II by any conventional hydrogenation method as hereinbefore described for hydrogenating carbon-carbon double bonds, followed by removal of the protecting group designated R in the compound of formula V or IV. The protecting group may be removed by methods as hereinbefore described.

The following Examples are meant to further illustrate, but not limit, the invention in scope or spirit.

EXAMPLE 1

4,8,12-Trimethyltridec-2-yn-1,4-diol

Into a 2-liter, three-neck, round-bottom flask fitted with a mechanical stirrer, a reflux condenser, and an addition funnel was added 210 g (3.60 mol) of finely powdered potassium hydroxide and 500 ml of anhydrous tetrahydrofuran. The resulting reaction mixture was heated to reflux and then 30.0 g (0.54 mol) of propargyl alcohol was slowly added over a 30 minute period with rapid stirring. The mixture was refluxed for 3 hours before 100 g (0.51 mol) of hexahydropseudoionone in 140 ml of tetrahydrofuran was slowly added over a 2-hour period. After an additional 2 hours at reflux, the reaction was cooled to 0° C. and poured onto 1000 g of ice and 360 g of concentrated sulfuric acid with efficient mixing. The resulting aqueous layer was rinsed with 3×100 ml of ether and the combined organic layers were rinsed with 50 ml of water, 3×50 ml of saturated aqueous sodium bicarbonate, and 50 ml of brine. The resulting ethereal solution was dried with 50 g of magnesium sulfate, and the solvent was removed at aspirator pressure with the aid of a rotary evaporator, leaving 110 g of crude product. Vacuum distillation at 40 μHg and 140° C. afforded 92 g (73%) of pure product, i.e. 4,8,12-trimethyltridec-2-yn-1,4-diol.

EXAMPLE 2

4,8,12-Trimethyltridecanol

A 2000 ml, three-neck, round-bottom flask was fitted with an addition funnel, a mechanical stirrer, and a Dean-Stark trap capped with a reflux condenser and a static argon inlet. The flask was flamed dried and upon cooling, 75 g (0.55 mol) of finely ground, freshly fused potassium bisulfate was added followed by 750 ml of p-xylene. The resulting mixture was heated to reflux before 100 g (0,44 mol) of 4,8,12-trimethyltridec-2-yn-1,4-diol in 300 ml of p-xylene was rapidly added. The resulting dark-brown mixture was rapidly stirred under reflux for 4 hours until gas liquid phase chromatographic (glpc) analysis on 10% carbowax 20M indicated 5% of starting material remained. The mixture was cooled to 0° C. and poured into 200 ml of water and was extracted with 5×300 ml of ether. The combined ether layers were washed with 2×100 ml of water, 4×50 ml of saturated sodium bicarbonate, 2×50 ml of water, and was dried with 70 g of magnesium sulfate. The solvent was removed at reduced pressure with rotary evaporator. The resulting brown oil was distilled at 50 μHg and 80°-100° C. to afford 60 g of a mixture dehydration products. The 60 g (0.25 mol) of product was dissolved in 300 ml of absolute ethanol and was added to 30 g of Raney nickel in a 600 mL glass autoclave liner. The mixture was heated at 80° C. under 1900 psi hydrogen for 5 hours. The reaction was cooled to room temperature, filtered, and the solvent was removed at reduced pressure with a rotary evaporator. Distillation afforded 51.7 g of product, i.e. 4,8,12-trimethyltridecanol, as a clear liquid: bp 119°-122° C. at 2 mm Hg.

EXAMPLE 3

1-Bromo-4,8,12-trimethyltridecane

Into a 250 ml, three-necked, round-bottom flask equipped with a thermometer, serum cap, argon blubber and a magnetic stir bar was added 10 g (40 mmol) of 4,8,12-trimethyltridecanol, 30 ml of purified dimethylformamide (DMF) (stored over calcium sulfate prior to distillation) and 11.2 g (43 mmol) of triphenylphosphine. The solution was cooled to 0° C. before 2.19 ml (43 mmol) of bromine was added via syringe at such a rate that the temperature remained below 30° C. At the end of the addition a persistent orange color remained. The reaction was poured into 200 ml of hexane and 200 ml of water. The aqueous layer was extracted 3×200 ml of hexane. The combined organic layers were rinsed with 300 ml of saturated sodium bicarbonate, 100 ml brine, and were dried with 80 cc of sodium sulfate. The solvent was removed at reduced pressure with a rotary evaporator to afford a mixture of oil and solid. The mixture was triturated with hexane and filtered over a short plug of 40 g of silica gel eluting with hexane. Removal of the solvent left 10.7 g of colorless oil. Distillation through a 10 cm, vacuum jacqueted vigreaux afforded 9.7 g of colorless product, i.e. 1-bromo-4,8,12-trimethyltridecane, bp 119°-20° C. at 0.15 mm Hg.

EXAMPLE 4

4,8,12-Trimethyltridecyl triphenylphosphonium bromide

Into a 500 ml, three-necked, round-bottom flask equipped with a reflux condenser, a magnetic stir bar, and a static argon inlet, was placed 5.90 g (24 mmol) of the 1-bromo-4,8,12-trimethyltridecane and 6.64 g (25 mmol) of triphenylphosphine. The resulting mixture was stirred in an oil bath at 180° C. overnight (19 hours). The resulting phosphonium salt, i.e. 4,8,12-trimethyltridecyl, was used without further purification or storage.

EXAMPLE 5

Preparation of a mixture of (Z)-3,5,6-trimethyl-4-(phenylmethoxy)-2-(3,7,11,15-tetramethyl--3-decahexen-1-yl)phenol and (E)-3,5,6-trimethyl-4-(phenylmethoxy)-2-(3,7,11,15-tetramethyl-3-decahexen-1-yl)phenol Into the 500 ml, round-bottom flask containing the phosphonium salt prepared in Example 4 was added 75 ml of anhydrous tetrahydrofuran. The resulting solution was cooled to −20° C. and 10.8 ml (24.3 mmol) of 2.25M n-butyllithium in hexane was slowly added,. The cooling bath was removed and the reaction was allowed to warm to 20° C. before it was cooled back to 0° C. A solution of 3.79 g (12.2 mmol) of 6-benzyloxy-2-hydroxy-2,5,7,8-tetramethylchroman in 50 ml of anhydrous tetrahydrofuran was slowly added. The resulting reaction was then allowed to warm to room temperature before it was refluxed for 3½ hours. The reaction was cooled to ambient temperature and partitioned between 125 ml of saturated aqueous ammonium chloride and 250 ml of ether. The resulting organic layer was successively rinsed with 125 ml of saturated ammonium chloride and then 125 ml of brine. The organic layer was dried over 50 cc of sodium sulfate and the solvent was removed at reduced pressure with the aid of a rotary evaporator. The resulting oil was chromatographed on 120 g of silica gel 60 (70–230 mesh) using 1:1 toluene-ethyl acetate to afford 3.7 g of a mixture of E- and Z-isomeric products. Analytic high pressure liquid chromatography (HPLC) (column P7, 50 cm A7, mobile phase 2% tetrahydrofuran in heptane, detector 254 nm) indicated a 5:2 mixture of the E- and Z-isomers.

EXAMPLE 6

HPLC Separation of E- and Z-Isomeric Compounds

A mixture of 4.5 g (8.6 mmol) of the E and Z olefinic isomers obtained by the procedure of Example 5, which isomers by glpc analysis (1M, 3% OV-17) consisted of a 2.6 to 1 ratio, were subjected to HPLC separation on 12 ft×1" silica gel column. Two pure fractions were collected of 1.1 g and 2.9 g. By both HPLC and glpc analysis these fractions consisted of a single component. Based on CMR analysis of these fractions, the major fraction was assigned the E configuration around the double bond and the minor fraction was assigned the Z configuration.

EXAMPLE 7

Preparation of a mixture of
(Z)-4-acetyloxy-2-(3,7,11,15-tetramethyl-3-hexadecenyl-3,5,6-trimethylphenol and
(E)-4-(acetyloxy)-2-(3,7,11,15-tetramethyl-3-hexadecenyl)-3,5,6-trimethylphenol Under an atmosphere of argon with magnetic stirring, the phosphonium salt as prepared in Example 4 from 9.5 g (0.039 mol) of bromide and 10.7 g (0.041 mol) of triphenylphosphine was dissolved in 150 ml of anhydrous tetrahydrofuran and cooled to −20° C. To the resulting cold solution was slowly added 15.3 ml (0.35 mol) of 2.3M n-butyl lithium in hexane. The cooling bath was removed and the resulting reaction was allowed to warm to 20° C. before recooling it to −15° C. and slowly adding a solution of 5.2 g (0.020 mol) of 6-acetoxy-2-hydroxy-2,5,7,8-tetramethylchroman in 100 ml of tetrahydrofuran. The reaction was allowed to warm to ambient temperature and then was refluxed for 4 hours. The resulting mixture was cooled to ambient temperature and partitioned between 250 ml of saturated ammonium chloride and 350 ml of ether. The resulting organic layer was washed successively with 250 ml of saturated, aqueous sodium bicarbonate and then 250 ml of brine. The resulting ethereal solution was dried with 80 cc of sodium sulfate and the solvent was removed at reduced pressure with a rotary evaporator. The resulting oil was chromatographed on 150 g of silica gel 60 (70–230 mesh) using hexane and 10% ethyl acetate in hexane as the eluent to afford 5.3 g of a mixture of product as the E- and Z-stereoisomers. The isomers were partially separated into two pure fractions via HPLC on a Waters Prepak 500 silica gel column using 2% tetrahydrofuran in heptane as the eluent. The major fraction (2.0 g) was assigned the E-configuration about the double bond by CMR and the minor fraction (1.0 g) was assigned the Z-configuration.

EXAMPLE 8

Preparation of Vitamin E from
(Z)-3,5,6-trimethyl-4-(phenylmethoxy)-(2-(3,7,11,15-tetramethyl-3-decahexen-1-yl)phenol (a) Cyclization A Fisher-Porter bottle containing 21.7 mg (0.096 mmol) of palladium acetate, 15.2 μl (0.096 mmol) of (−)-β-pinene, 10 ml of isopropanol, 191.6 mg (0.96 mmol) of cupric acetate hydrate, and 500 mg (0.96 mmol) of (Z)-3,5,6-trimethyl-4-(phenylmethoxy)-2-(3,7,11,15-tetramethyl-3-decahexen-yl-phenol was pressurized to 15 psi with oxygen and stirred in an oil bath at 35° C. for 19 hours. The resulting reaction was cooled to room temperature and partitioned between 40 ml of ethyl acetate and 30 ml of water. The resulting orgahic layer was washed with 30 ml of brine, dried with 10 cc of magnesium sulfate, and the solvent was removed at reduced pressure. The resulting oil was chromatographed on 5 g of silica gel 60 (70–230 mesh) eluting with 2:1 hexane:toluene to afford as product 259 mg (54%) of 1'-dehydro Vitamin E benzyl ether.

(b) Hydrogenation

The product obtained above was dissolved in 8 ml of ethyl acetate and was transferred to a Fisher-Porter bottle containing 51.8 mg of 10% palladium on carbon. The vessel was pressurized to 50 psi with hydrogen and stirred at ambient temperature overnight (19 hours). The catalyst was filtered from the solution and the solvent was removed at reduced pressure to afford 200 mg of Vitamin E.

(c) Determination of optical purity at the 2-center

The 200 mg of Vitamin E obtained according to (a) and (b) of Example 8 was dissolved in 4 ml of hexane and 4 ml of a potassium ferricyanide solution (prepared from 1 g of potassium ferricyanide in 10 ml of 0.2N sodium hydroxide) was added. The resulting reaction mixture was vigorously stirred for ½ before it was rinsed with 20 ml of water and 20 ml of brine. The resulting solution was dried with 5 cc of sodium sulfate and the solvent was removed at reduced pressure to provide a yellow oil. The oil was purified via preparation silica gel TLC using hexane:ether (19:1) as the eluent. The yellow band was collected to afford 76 mg of yellow oil, $[\alpha]_{25}^{D} = -2.63$, [c=1.9, isooctane]. Since (2S,4'RS,8'RS)-α-tocopherol dimer has a rotation of −23.6° under identical conditions, the above product has an enantiomeric excess of 11.2% at the 2-center.

EXAMPLE 9

Preparation of Vitamin E from
(Z)-4(acetyloxy)-2-(2,7,11,15-tetramethyl-3-hexadecenyl)-3,5,6-trimethylphenol (a) Cyclization The cyclization was on 100 mg (0.21 mmol) of (Z)-4-(acetyloxy)-2-(3,7,11,15-tetramethyl-3-hexadecenyl)-3,5,6-trimethylphenol following the procedure in Example 8(a) to afford 98 mg of crude 1'-dehydro Vitamin E acetate before chromatography.

(b) Hydrogenation

This crude cyclized product was hydrogenated following the procedure in Example 8(b) to afford 89 mg of crude Vitamin E acetate.

(c) Removal of the acetate

Under an argon atmosphere the 89 mg of the crude Vitamin E acetate obtained by the procedure of Example 9(b) was dissolved in 3 ml of anhydrous tetrahydrofuran and was cooled to $-30°$ C. To the resulting cooled solution was added 0.43 ml (0.78 mmol) of a 1.8M methyl lithium solution in ether. The resulting mixture was allowed to warm to $0°$ C. before it was quenched with 15 ml of saturated aqueous ammonium chloride solution. The mixture was extracted with $2\times 20$ ml of ether and the resulting ethereal layers were combined and dried with 5 cc of sodium sulfate and the solvent was removed at reduced pressure to provide 71 mg of crude Vitamin E.

(d) Determination of the optical purity at the 2-center

The 71 mg of crude Vitamin E obtained by the procedure of Example 9(c) was oxidized following the procedure of Example 8(c) and purified by preparative thin lower chromatography (TLC) to afford 20 mg of dimer, $[\alpha]_{25}{}^D = -0.95$, [c=1.9, isooctane]. This corresponds to an optical purity of 4.0% at the 2-center.

EXAMPLE 10

2-Methylene-1,7,7-trimethylbicyclo[2,2,1]heptane

Into a dry three-neck, 250 ml round-bottom flask was placed 1.2 g (50 mmol) of an oil dispersion of sodium hydride. The flask was flushed with argon before 25 ml of dimethylsulfoxide freshly distilled from calcium hydride was slowly added. The resulting mixture was heated in a $75°$ C. oil bath for 45 minutes until gas evolution ceased. The mixture was cooled to $0°$ C. and a solution of 17.85 (50 mmol) of methyltriphenylphosphonium bromide in 50 ml of dimethylsulfoxide was added. The resulting green-yellow solution was stirred at ambient temperature for 10 minutes before 6.08 g (40 mmol) of $(-)$-camphor($[\alpha]_D{}^{25}=38.3$ (c=1.18, CH$_3$OH)) in 20 ml of dimethylsulfoxide was added. The resulting reaction was stirred in a $55°$ C. oil bath overnight (19 hours). Upon cooling to room temperature 40 ml of water were added and the aqueous layer was extracted with $3\times 50$ ml of pentane. The resulting organic layer was also extracted $2\times 50$ ml of pentane and the combined pentane layers were rinsed with 100 ml of an equal volume solution of water and dimethylsulfoxide. The resulting organic layer was dried over 50 cc of sodium sulfate and the solvent was quickly removed at aspirator pressure to provide a mixture of oil and solid. The mixture was chromatographed on 35 g of silica gel eluting with hexane to afford 3.0 g of product, i.e. 2-methylene-1,7,7-trimethylbicyclo[2,2,1]heptane, contaminated with hexane. Sublimation at $25°$ C. and 1 mm produced 1.5 g of colorless solid: mp $69\sqrt{\ }-70°$; $[\alpha]_D{}^{25}=39.54$ (c=4,4, CH$_3$OH).

EXAMPLE 11

Palladium (II) trifluoroacetate

Into 40 ml of distilled trifluoroacetic acid was dissolved 1.0 g of palladium acetate. The solvent was distilled off and an additional 20 ml of trifluoroacetic acid was added and distilled off. The residual solid was dried in facuo at $40°$ C. to afford 1.3 g of brown product, i.e. palladium (II) trifluoroacetate, mp $210°$ C. (dec).

EXAMPLE 12

π-Allyl palladium (II) complex between palladium trifluoroacetate and $(-)$-β-pinene Under an argon atmosphere 350 mg (1.16 mmol) of palladium trifluoroacetate was dissolved in 10 ml of acetone before 0.18 ml (1.2 mmol) of $(-)$-β-pinene was added. After stirring at room temperature for 30 minutes, the resulting reaction was concentrated at aspirator pressure with the aid of a rotary evaporator. The resulting oil was triturated with hexane and the crystals were collected, washed with hexane, and dried in vacuo to afford 300 mg of product, i.e. the π-allyl palladium (II) complex, mp $116°$-$8°$ C. (dec).

What is claimed is:

1. A compound of the formula

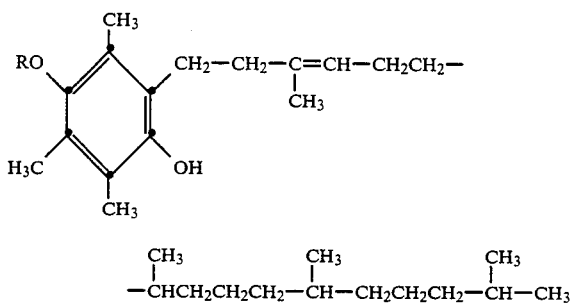

wherein R is hydrogen, or when taken together with its attached oxygen atom, an ester protecting group removable by hydrolysis or an ether protecting group removable by hydrogenolysis or acid catalyzed cleavage.

2. A compound according to claim 1 which is (Z)-3,5,6-trimethyl-4-phenylmethoxy)-2-(3,7,11,15-tetramethyl-3-decahexen-1-yl)phenol.

3. A compound according to claim 1 which is (E)-3,5,6-trimethyl-4-(phenylmethoxy)-2-(3,7,11,15-tetramethyl-3-decahexen-1-yl)phenol.

4. A compound according to claim 1 which is (Z)-4-(acetyloxy)-2-(3,7,11,15-tetramethyl-3-hexadecenyl)-3,5,6-trimethylphenol.

5. A compound according to claim 1 which is (E)-4-(acetyloxy)-2-(3,7,11,15-tetramethyl-3-hexadecenyl)-3,5,6-trimethylphenol.

* * * * *